(12) United States Patent
Buriat et al.

(10) Patent No.: US 11,383,032 B2
(45) Date of Patent: Jul. 12, 2022

(54) METHOD AND SYSTEM FOR PERFORMING A CONTINUOUS INFUSION PROCESS

(71) Applicant: Fresenius Vial SAS, Brézins (FR)

(72) Inventors: Maxime Buriat, Genilac (FR); Alexandre Guerrini, Seyssinet-Pariset (FR)

(73) Assignee: Fresenius Vial SAS, Brézins (FR)

( * ) Notice: Subject to any disclaimer, the term of this patent is extended or adjusted under 35 U.S.C. 154(b) by 454 days.

(21) Appl. No.: 15/736,083

(22) PCT Filed: Jun. 13, 2016

(86) PCT No.: PCT/EP2016/063479
§ 371 (c)(1),
(2) Date: Dec. 13, 2017

(87) PCT Pub. No.: WO2017/012781
PCT Pub. Date: Jan. 26, 2017

(65) Prior Publication Data
US 2018/0185574 A1 Jul. 5, 2018

(30) Foreign Application Priority Data
Jul. 20, 2015 (EP) ..................................... 15306177

(51) Int. Cl.
*A61M 5/168* (2006.01)
*A61M 5/145* (2006.01)
*A61M 5/172* (2006.01)

(52) U.S. Cl.
CPC ...... *A61M 5/16827* (2013.01); *A61M 5/1452* (2013.01); *A61M 5/172* (2013.01)

(58) Field of Classification Search
CPC ............ A61M 5/16827; A61M 5/1452; A61M 5/172; A61M 5/1407; A61M 5/1408;
(Continued)

(56) References Cited

U.S. PATENT DOCUMENTS 9,814,834 B2 11/2017 Ali et al.
2004/0254525 A1 12/2004 Uber, III et al.
(Continued)

FOREIGN PATENT DOCUMENTS

CN 101848741 9/2010
JP H6-277283 10/1994
(Continued)

OTHER PUBLICATIONS

International Search Report and Written Opinion, counterpart International Appl. No. PCT/EP2016/063479, dated Jul. 27, 2016 (16 pages).
(Continued)

*Primary Examiner* — Kevin C Sirmons
*Assistant Examiner* — Leah J Swanson
(74) *Attorney, Agent, or Firm* — Cook Alex Ltd.

(57) ABSTRACT

A method for performing a continuous infusion process includes delivering a first fluid through a first delivery line at a first flow rate using a first infusion device in a first phase, and delivering a second fluid through a second delivery line at a second flow rate using a second infusion device in a second phase following the first phase. A relay device connected to said first and second delivery lines configured to discharge first or second fluid to an outlet delivery line connected to the relay device, the outlet delivery line having a predefined delivery volume. Subsequent to the delivery of the first fluid in the first phase, the second infusion device in an intermediate phase is operated for a predetermined delivery time to deliver the second fluid at the first flow rate, the predetermined delivery time determined taking the predefined delivery volume into account.

10 Claims, 6 Drawing Sheets

(58) Field of Classification Search
CPC ...... A61M 2005/1787; A61M 5/16877; A61M 5/16881
See application file for complete search history.

(56) References Cited

U.S. PATENT DOCUMENTS

| | | |
|---|---|---|
| 2005/0197649 A1 | 9/2005 | Shelton et al. |
| 2006/0224140 A1 | 10/2006 | Junker |
| 2007/0106208 A1 | 5/2007 | Uber, III et al. |
| 2007/0197963 A1 | 8/2007 | Griffiths et al. |
| 2008/0269678 A1 | 10/2008 | Rebours |
| 2008/0294096 A1 | 11/2008 | Uber, III et al. |
| 2009/0221986 A1 | 9/2009 | Wang et al. |
| 2010/0312039 A1 | 12/2010 | Quirico et al. |
| 2011/0087189 A1 | 4/2011 | Jacobson et al. |
| 2011/0209764 A1* | 9/2011 | Uber .................... A61N 5/1007 137/1 |
| 2013/0028841 A1 | 1/2013 | Yagi et al. |
| 2013/0184676 A1 | 7/2013 | Kamen et al. |
| 2013/0218080 A1 | 8/2013 | Peterfreund et al. |
| 2015/0133188 A1 | 5/2015 | Chang et al. |

FOREIGN PATENT DOCUMENTS

| | | |
|---|---|---|
| JP | 2013-192890 | 9/2013 |
| RU | 2512939 | 4/2014 |
| WO | WO 01/80928 A2 | 11/2001 |
| WO | WO 2005/084273 A2 | 9/2005 |
| WO | WO 2009/149367 A1 | 12/2009 |
| WO | WO 2012/167090 A1 | 12/2012 |

OTHER PUBLICATIONS

Russian Patent Office (FIPS), translated Search Report for Russian counterpart application 2018106027/14 (dated Aug. 13, 2019) (2 pages).
Russian Patent Office (FIPS), translated Official Action for Russian counterpart application 2018106027/14 (circa Sep. 2019) (6 pages).

* cited by examiner

METHOD AND SYSTEM FOR PERFORMING A CONTINUOUS INFUSION PROCESS

The present application is a U.S. National Stage of PCT International Patent Application No. PCT/EP2016/063479, filed Jun. 13, 2016, which claims priority to EP Application No. 15306177, filed Jul. 20, 2015, both of which are hereby incorporated herein by reference.

The invention relates to a method and system for performing a continuous infusion process using at least two infusion devices.

Within a method of this kind in a first phase a first fluid from a first medication container is delivered through a first delivery line at a first flow rate using a first infusion device. After the first medication container has been depleted or nearly depleted, the infusion is taken over by a second infusion device so that in a second phase the second infusion device delivers a second fluid from a second medication container through a second delivery line at a second flow rate. The first delivery line and the second delivery line both are connected to a relay device, which is constituted to receive the first fluid via the first delivery line in the first phase and the second fluid via the second delivery line in the second phase. The relay device discharges the fluid it receives to an outlet delivery line, via which infusion into a patient may take place.

A method of this kind is for example known from US 2008/0269678 A1. Herein, two infusion devices in the shape of syringe pumps are applied in a concerted fashion in order to achieve a continuous infusion process, the infusion devices being connected via delivery lines to a coupler and via the coupler to a common infusion line. When a first medication container is depleted or nearly depleted, a controller automatically executes a relay function, sending control signals and instructing a first driver of the first infusion device to cease administration of a fluid from the first medication container and a second driver of the second infusion device to begin administration of a fluid from a second medication container in a closely-timed sequence.

A method of this kind may for example be used for the so called catecholamine infusion. Within the catecholamine infusion, medication such as adrenaline, noradrenaline or dobutamine may be administered to a patient for example for the purpose of resuscitation. Medication in this context is generally administered intravenously at a rather low dose rate, wherein it must be taken care that the dose rate is stable and continuous, because otherwise blood pressure and heart frequency peaks or drops may occur due to peaks or drops in the dose rate of the administered medication.

A system of multiple infusion devices may be used to continuously administer a medication to a patient over a comparatively long period of time at a constant dose rate. For this, however, it is necessary that the infusion devices are operated in a controlled, concerted fashion such that, upon depletion of a medication container associated with a first infusion device, infusion by a second infusion device from a second medication container starts in order to insure a continuous, non-interrupted infusion process.

In this regard, however, due to the length of the delivery lines connected to the infusion devices a second medication from a second infusion device may not immediately be delivered to a patient upon stopping the infusion by a first infusion device and starting the infusion by the second infusion device. This is due to the fact that during infusion by the first infusion device the outlet delivery line connecting the relay device with the patient is filled by the medication stemming from the first medication container associated with the first infusion device such that, upon starting infusion by the second infusion device, at first the residual medication from the first medication container in the outlet delivery line will be administered to the patient. This however may be problematic if the flow rate of the second infusion device is different than the flow rate of the first infusion device, leading to an increase or decrease in the dose rate by which the residual medication in the outlet delivery line is delivered to the patient.

There is, hence, a desire for a method and a system which reliably ensure that upon switching infusion from a first infusion device to a second infusion device a constant dose rate can be obtained.

Within a fluid infusion system as described in US 2011/0087189 A1 a fluid infusion pump discharges a fluid to a test subject in accordance with an infusion routine including for example a rate, a volume, a starter time, an end time and a duration.

In a system known from US 2013/0218080 A1 drugs are mixed with a carrier fluid using a multiplicity of infusion devices connected to a flow junction structure, via which the mixed fluid is delivered for example to a patient.

It is an object of the instant invention to provide a method and system for performing a continuous infusion process using at least two infusion devices, the method and system allowing for a continuous infusion at a desired, in particular constant dose rate in particular when switching from one infusion device to another.

This object is achieved by means of a method comprising the features of claim 1.

Accordingly, within the method the second infusion device is operated in an intermediate phase, subsequent to the delivery of the first fluid using the first infusion device in the first phase, for a predetermined delivery time to deliver the second fluid at the first flow rate, the predetermined delivery time being determined by taking the predefined delivery volume of the outlet delivery line into account.

The method starts from the finding that a residual volume of the first fluid remains in the outlet delivery line upon termination of the first phase, namely after terminating the first infusion device to deliver the first fluid from the first medication container through the first delivery line (for example due to the first medication container being depleted or being nearly depleted).

If in this case—with the residual first fluid being present in the outlet delivery line—the second infusion device takes over the infusion and would deliver the second fluid from the second medication container at the second flow rate, this would cause the residual first fluid in the outlet delivery line to be administered to the patient at the second flow rate, which may be different than the first flow rate. If the second flow rate for example is larger than the first flow rate, this would cause an increased dose rate by which the residual first fluid in the outlet delivery line is delivered to the patient. If in turn the second flow rate is smaller than the first flow rate, the residual first fluid in the outlet delivery line would be administered to the patient at a reduced dose rate.

In order to overcome a change in dose rate by which the residual first fluid in the outlet delivery line is administered to the patient, the second infusion device, upon taking over the infusion process, for a predefined delivery time is operated at the first flow rate, i.e., at the flow rate of the first infusion device. This causes the residual first fluid in the outlet delivery line to be administered to the patient at the same flow rate at which the first infusion device has been operated, such that no change in dose rate occurs when the second infusion device starts its infusion operation.

The second infusion device is operated at the first flow rate for the predetermined delivery time. The predetermined delivery time herein is determined by taking into account the delivery volume of the outlet delivery line, i.e., the volume of the line in which residual first fluid is present after termination of the infusion operation of the first infusion device. The delivery volume of the outlet delivery line indicates the fluid capacity of the outlet delivery line. At termination of the infusion by the first infusion device the outlet delivery line is (completely) filled with the first fluid delivered by the first infusion device. The predetermined delivery time hence is determined as that time that is necessary to deplete the outlet delivery line of the residual first fluid at the first flow rate.

In the intermediate phase the second infusion device hence is operated at the first flow rate, i.e., at the flow rate of the first infusion device. At the end of the intermediate phase, i.e., after the outlet delivery line has been depleted of the residual first fluid, the second infusion device is switched to the second flow rate by which the second fluid is to be delivered for administration to the patient.

The first fluid and the second fluid may for example comprise the same medication, but at a different concentration. In order to ensure a constant dose rate (the dose rate equals the flow rate times the concentration of medication in the fluid) throughout the entire infusion process, hence, the flow rates by which the different infusion devices are operated ought to be different. For example, if the concentration of the medication in the first fluid is four times larger than in the second fluid, the first flow rate is by a factor of four smaller than the second flow rate. Upon switching to the second infusion device, hence, the flow rate is increased in order to deliver the second fluid from the second medication container associated with the second infusion device at an increased flow rate, such that the same dose rate as during infusion by means of the first infusion device is achieved.

The object is also achieved by means of a system for performing a continuous infusion process using at least two infusion devices. The system comprises: a first infusion device constituted to deliver a first fluid from a first medication container through a first delivery line at a first flow rate in a first phase; a second infusion device constituted to deliver a second fluid from a second medication container through a second delivery line at a second flow rate in a second phase following the first phase; and a relay device connected to said first delivery line and said second delivery line and constituted to receive the first fluid via the first delivery line in the first phase and the second fluid via the second delivery line in the second phase. The relay device is further constituted to discharge the received first or second fluid to an outlet delivery line connected to the relay device for administration to a patient, the outlet delivery line having a predefined delivery volume.

According to the proposed solution, the system is constituted such that, subsequently to the delivery of the first fluid using the first infusion device in the first phase, the second infusion device in an intermediate phase is operated for a predetermined delivery time to deliver the second fluid at the first flow rate, the predetermined delivery time being determined taking the predefined delivery volume of the outlet delivery line into account.

The advantages and advantageous embodiments described above for the method equally apply also to said system.

A method and a system of this kind are for example applicable for a catecholamine infusion in which substances belonging to the group of dopamines and its derivates are infused to a patient. A medication used in this regard can for example comprise dopamine, noradrenaline or adrenaline. The infusion of such medication can be used for example in the intensive care and emergency medicine for resuscitation of a patient or the like. The medication is infused intravenously to a patient, wherein a stable, steady infusion of the medication at a constant dose rate is desired in order to avoid peaks or drops of the dose rate, which otherwise may lead to peaks or drops in the blood pressure or the heart frequency of the patient.

In one embodiment, the first infusion device and the second infusion device each comprise a processor, wherein the first infusion device and the second infusion device are in communication connection with each other for controlling the operation of the second infusion device in dependence of the operation of the first infusion device. If for example the first medication container associated with the first infusion device is depleted or is nearly depleted, a control signal may be issued by one of the processors which controls the second infusion device to start its infusion operation, while another control signal is issued that stops the first infusion device. The second infusion operation hence is performed in a concerted fashion following the first infusion operation such that a continuous infusion of medication to the patient can be obtained.

The infusion devices may be in communication connection with each other and may control each other to perform the continuous infusion operation. It however is also possible that an external control device is provided, which generates control signals and controls the operation of the first infusion device and the second infusion device.

In this regard it is to be noted that also more than two infusion devices could be present and can take part in the continuous infusion process. Hence, after the second medication container associated with the second infusion device is depleted or is nearly depleted the infusion operation can be continued by a third infusion device.

In this regard it further is to be noted that a continuous infusion operation involving more than two phases can also be obtained by reusing the infusion devices, for example by refilling or replacing the first medication container associated with the first infusion device after the first medication container has been emptied and after infusion has been taken over by the second infusion device.

To provide for a continuous infusion involving the multiple infusion devices, the infusion devices beneficially exchange information concerning for example their flow rates, the filling levels of their associated medication containers, their operational status such as start or stop signals, the type of fluids and their characteristics in their associated medication containers, wherein other or more information may be present and may be exchanged. One infusion device hence knows about the operational status of the other infusion device such that, for example, the second infusion device may determine the predefined delivery time at which it shall be run in the intermediate phase following infusion by the first infusion device according to the first flow rate and the delivery volume of the outlet delivery line.

The delivery volume (also denoted as dead volume) of the outlet delivery line can for example be input by a user to one or multiple infusion devices and hence is known to the first and/or the second infusion device. Or it can be predefined for an infusion set connected to the infusion devices, such that by recognition of the infusion set the delivery volume of the outlet delivery line is known to the infusion devices. Or the delivery volume of the outlet delivery line can be measured in an initial calibration step by measuring the volume of fluid that can be received in the outlet delivery line. Alternatively, an analysis of the pressure in the delivery lines could be performed by the infusion devices in order to draw conclusions about the volume of the outlet delivery line.

The method and system as described above may in particular make use of infusion devices in the shape of syringe pumps receiving a syringe and acting onto the syringe for delivering medication from a cylindrical tube of the syringe. In principle, however, the method and system may also make use of infusion devices such as peristaltic (volumetric) infusion pumps or other infusion devices, such that the invention is not limited to the use of syringe pumps.

The invention shall subsequently be described in more detail with regard to the embodiments shown in the Figures. Herein:

Figure 1:
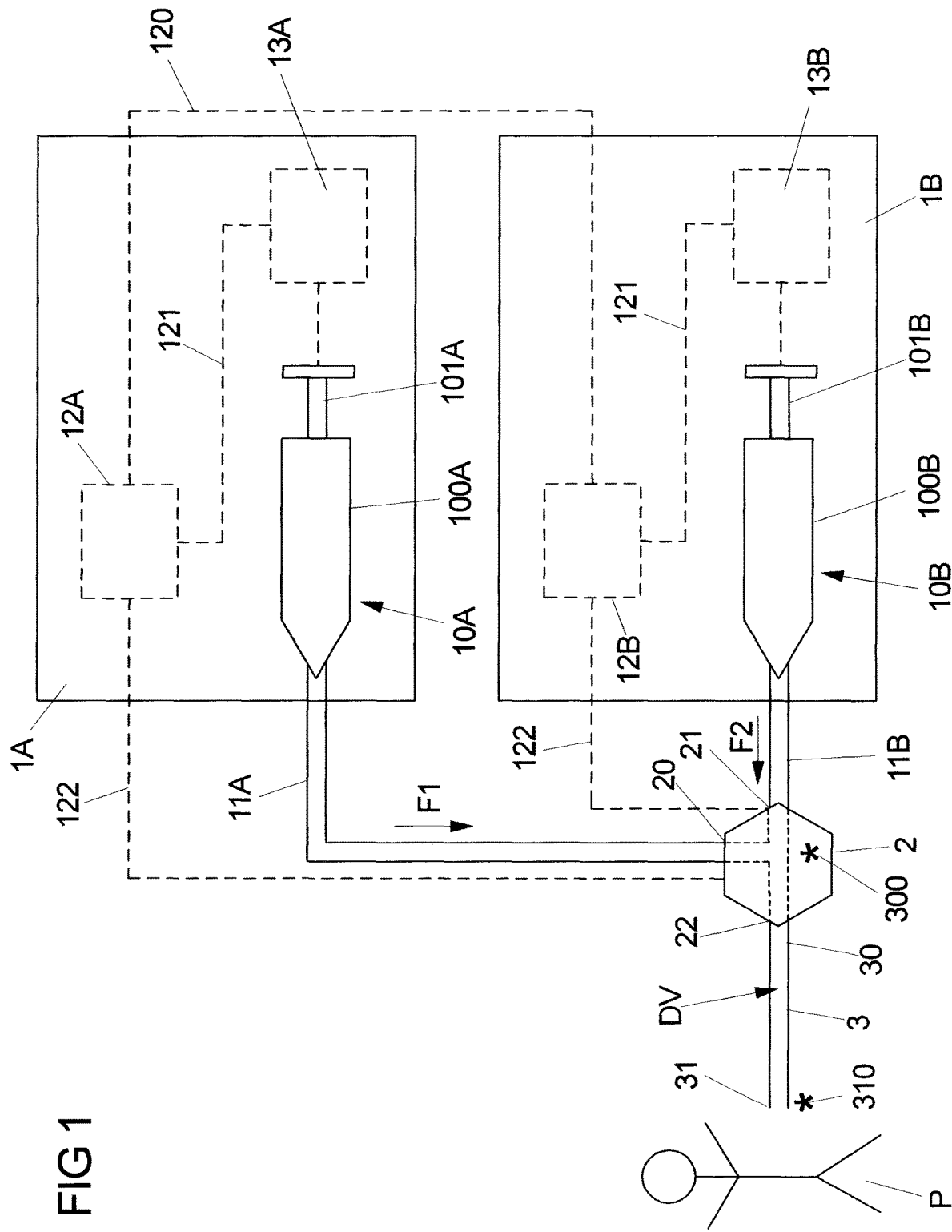
FIG. 1 shows a schematic view of a system comprising a multiplicity of infusion devices used for continuously infusing medication towards a patient.

FIG. 1 shows a schematic drawing of a system comprising, in the shown embodiment, two infusion devices 1A, 1B which each comprise a pump device 10A, 10B in the shape of a syringe for delivering a fluid from a medication container 100A, 100B through a delivery line 11A, 11B towards a patient P. Each pump device 10A, 10B shaped as a syringe comprises a cylindrical tube constituting the medication container 100A, 100B and a plunger 101A, 101B received in the cylindrical tube. The pump device 10A, 10B is received for example in a suitable holding device of the associated infusion device 1A, 1B constituted as a syringe pump and acting onto the plunger 101A, 101B of the associated syringe by means of an electric drive device 13A, 13B for continuously pushing the plunger 101A, 101B into the cylindrical tube 100A, 100B to deliver the fluid received in the cylindrical tube 100A, 100B at a constant flow rate towards the patient P.

The system is set up to perform a continuous infusion operation. For this, the delivery lines 11A, 11B are each connected to a common communication node in the shape of a relay device 2. The delivery lines 11A, 11B are connected to inlets 20, 21 of the relay device 2. The relay device 2 is constituted to receive fluid through the delivery lines 11A, 11B from the infusion devices 1A, 1B and to discharge a received fluid to an outlet delivery line 3 connected at an end 30 to an outlet 22 of the relay device 2. The outlet delivery line 3 may, for example, be connected to a patient P by means of a suitable injection needle or the like such that via the outlet delivery line 3 a fluid can be administered to the patient P.

Figure 2:
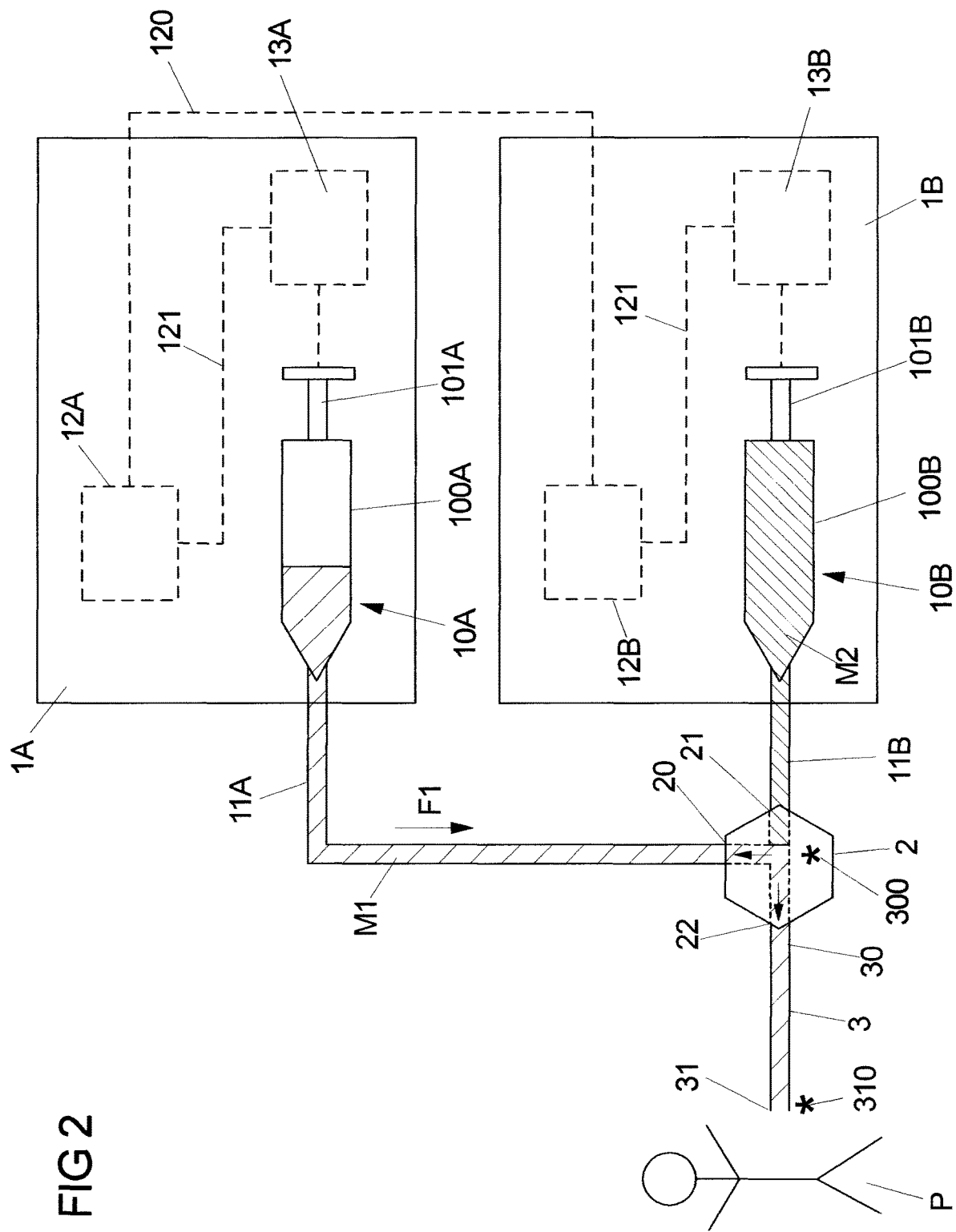
FIG. 2 shows the drawing of FIG. 1 in a first phase in which the infusion is carried out by a first infusion device.

The (continuous) infusion process starts, for example, in a first infusion phase with the first infusion device 1A delivering a fluid, in particular, a medication, from its medication container 100A via the delivery line 11A at a first flow rate F1. As illustrated in FIG. 2, the relay device 2 in this case lets the fluid M1 pass from the inlet 20 to the outlet 22 and hence provides a fluid connection between the delivery line 11A and the outlet delivery line 3 such that the fluid M1 is delivered to the patient P at the first flow rate F1.

Once the medication container 100A is depleted or nearly depleted, the infusion process shall be switched over to the second infusion device 1B. To control this switching process, both the first infusion device 1A and the second infusion device 1B each comprise a processor 12A, 12B, which are via a communication line 120 in communication with each other. Furthermore, the processors 12A, 12B are, via communication lines 121, in communication with the electric drive device 13A, 13B of the associated infusion device 1A, 1B and furthermore, via communication lines 122 (see FIG. 1), in connection with the relay device 2. At the end of the first infusion phase (when the first medication container 100A is depleted or nearly depleted) a control signal is issued by for example the processor 12A associated with the first infusion device 1A and communicated to the processor 12B of the second infusion device 1B, the control signal causing the operation of the first infusion device 1A to stop and at the same time the operation of the second infusion device 1B to start. At the same time, also the relay device 2 is switched (for example by switching a suitable flow switching means contained in the relay device 2) such that, now, a fluid connection between the inlet 21 and the outlet 22 is obtained, as this is illustrated in FIG. 3.

Figure 3:
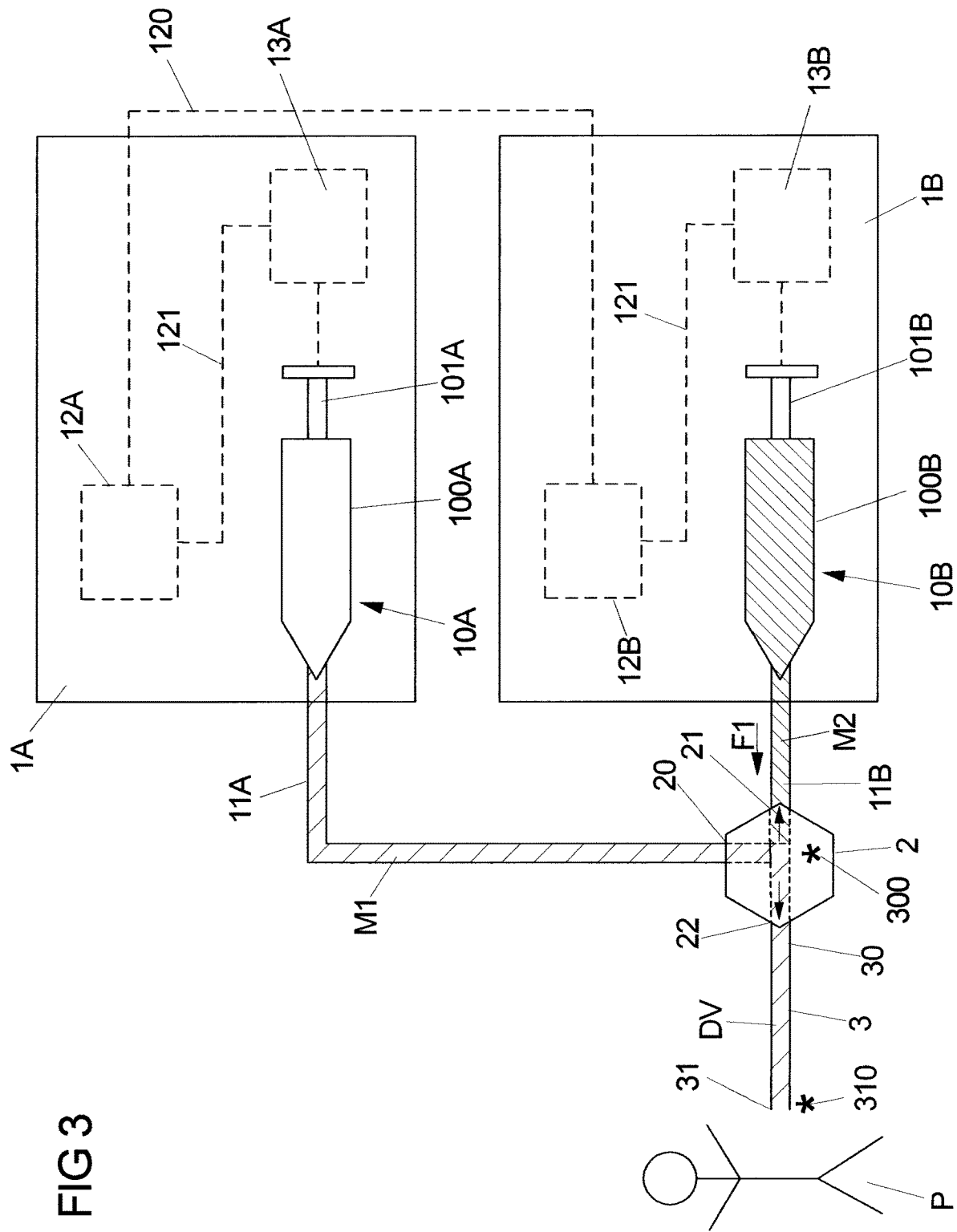
FIG. 3 shows the schematic drawing at the end of the first phase after depletion of a medication container of the first infusion device.

As is visible from FIG. 3, at the time the infusion process is switched over to the second infusion device 1B, a residual amount of the first fluid M1 delivered by the first infusion device 1A is still present in the outlet delivery line 3, more specifically between the two locations marked with the asterisks 300, 310 at the branch-off point within the relay device 2 on the one hand and the end 31 of the outlet delivery line 3 close to the patient P on the other hand. Upon start of the infusion operation of the second infusion device 1B, this residual volume of the first fluid M1 will be administered to the patient P prior to the second fluid M2 from the second medication container 100B associated with the second infusion device 1B entering into the outlet delivery line 3 and arriving at the patient P.

The first fluid M1 and the second fluid M2 may comprise the same medication, but, for example, at a different concentration. In order to ensure a constant dose rate, therefore, the first flow rate F1 of the first infusion device 1A and the second flow rate F2 of the second infusion device 1B differ. This can be expressed mathematically as follows:

$$\text{dose rate 1 (mg/h)} = \text{flow rate 1 (ml/h)} * \text{concentration 1 (mg/ml)}$$

$$\text{dose rate 2 (mg/h)} = \text{flow rate 2 (ml/h)} * \text{concentration 2 (mg/ml)}.$$

If the first dose rate and the second dose rate shall be equal (dose rate 1 (mg/h)=dose rate 2 (mg/h)), this means that the second flow rate is set as follows:

$$\text{flow rate 2 (ml/h)} = \text{flow rate 1 (ml/h)} * \text{concentration 1 (mg/ml)} / \text{concentration 2 (mg/ml)}.$$

If, for example, the concentration of medication in the first fluid M1 is twice the concentration of medication in the second fluid M2, the second flow rate F2 is to be chosen to be twice as large as the first flow rate F1 in order to obtain a constant dose rate.

However, if the infusion operation by means of the second infusion device 1B would be initiated with the second flow rate F2 immediately upon switching over the infusion process from the first infusion device 1A to the second infusion device 1B, this would lead to the residual volume of the first fluid M1 remaining in the outlet delivery line 3 to be administered to the patient P at the second flow rate F2, which would lead to a change in the dose rate (a peak or a drop in the dose rate), which may have disadvantageous effects on the patient P.

Figure 4:
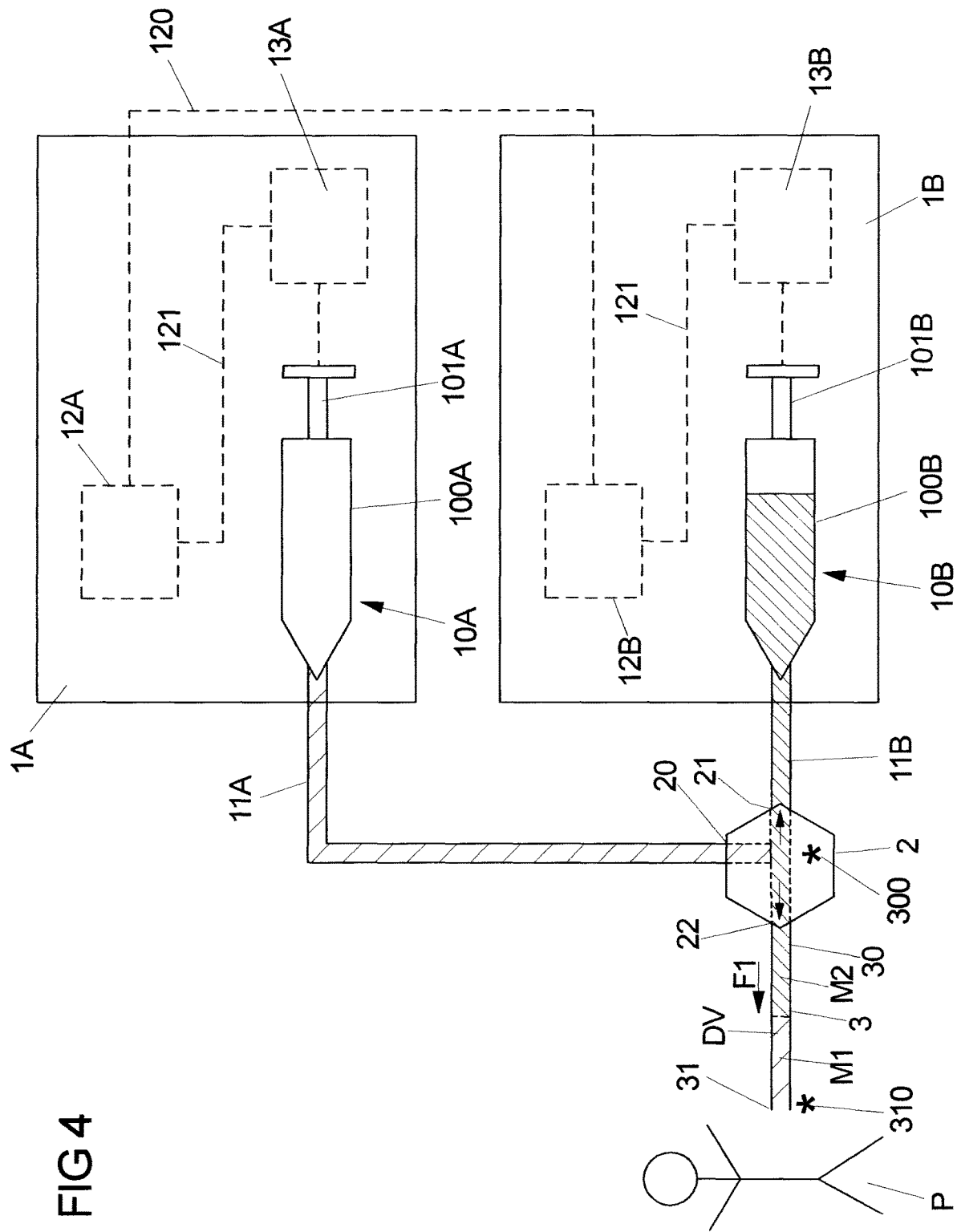
FIG. 4 shows the schematic drawing in an intermediate phase in which the infusion has been taken over by a second infusion device.

Therefore, when switching over the infusion process from the first infusion device 1A to the second infusion device 1B, in an intermediate phase the second infusion device 1B is operated to run at the first flow rate F1 for a predetermined delivery time, as it is indicated in FIGS. 3 and 4. The predetermined delivery time herein is determined by the delivery volume DV of the outlet delivery line 3 (including the flow path within the relay device 2 between the asterisk 300 and the outlet 22) and the first flow rate F1. Namely, the predetermined delivery time equals the delivery volume DV divided by the first flow rate F1:

$$T \text{ (h)} = \text{delivery volume DV (ml)/flow rate 1 (ml/h)}$$

$$= \text{delivery volume DV (ml)*concentration 1 (mg/ml)/dose rate 1 (mg/h)}$$

Figure 5:
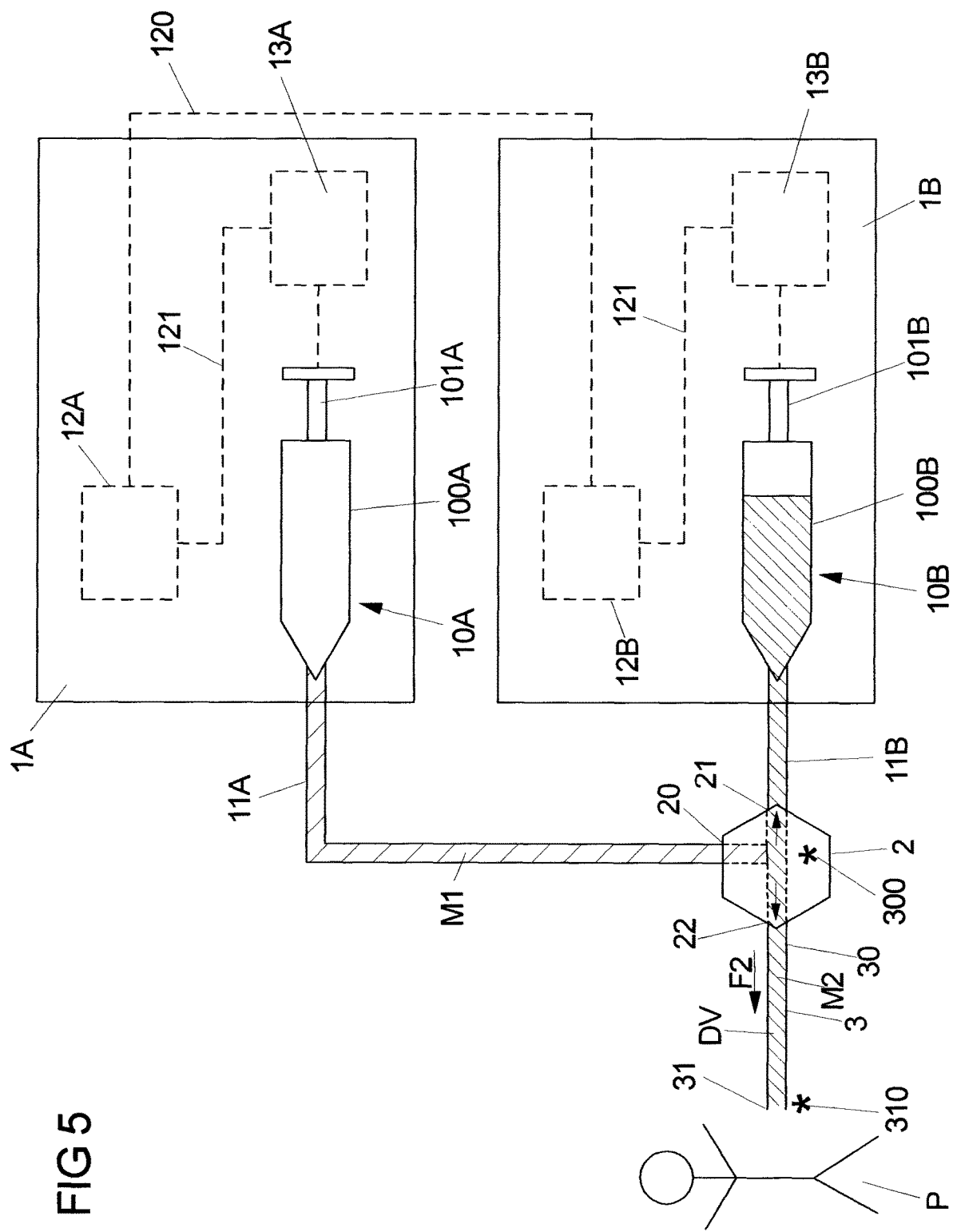
FIG. 5 shows the schematic drawing in a second phase in which the infusion is carried out by the second infusion device.

After the second infusion device 1B has been run for the predetermined delivery time T at the first flow rate F1, it is switched to the second flow rate F2, as indicated in FIG. 5. After lapse of the predetermined delivery time T the outlet delivery line 3 is depleted from the first fluid M1 stemming from the first medication container 100A associated with the first infusion device 1A and is filled with the second fluid M2 stemming from the second medication container 100B associated with the second infusion device 1B. The infusion process is then continued at the second flow rate F2, until the second medication container 100B is depleted or nearly depleted, upon which it can be switched over to another, third infusion device or it can be switched back to the first infusion device 1A whose medication container 100a has been refilled or replaced.

By means of the instant method and the instant system it can be assured that a dead volume of residual fluid in the outlet delivery line 3 is not delivered to the patient P at an increased or decreased flow rate differing from the flow rate by which the fluid should be delivered. Hence, a continuous infusion at a constant, unchanged flow rate can be ensured even when switching between different infusion devices for infusing different medicational fluids.

Figure 6:
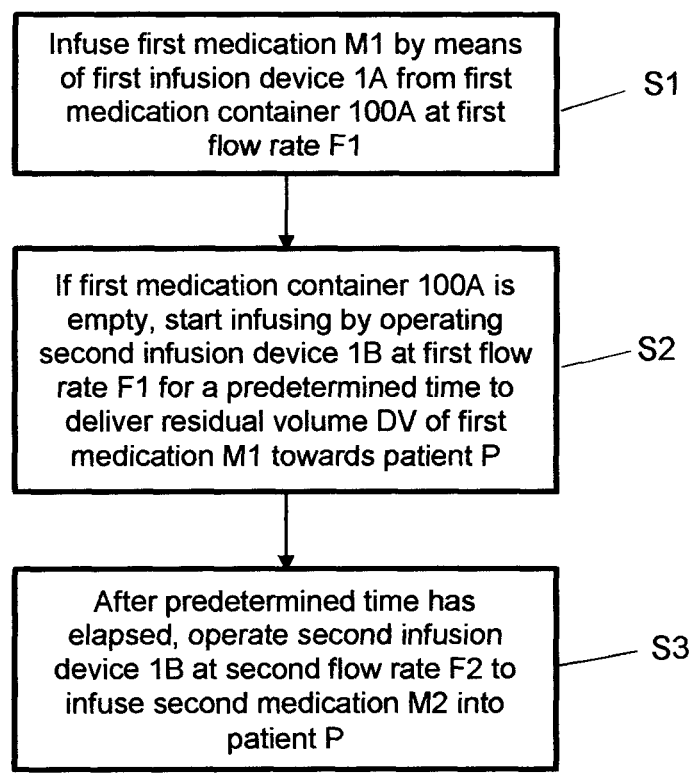
FIG. 6 shows a schematic flow diagram of the principle method steps for carrying out the continuous infusion process.

The method of the instant invention is summarized in the flow chart of FIG. 6.

Namely, in a first step S1 a first medication M1 is infused to a patient by means of a first infusion device 1A from a first medication container 100A at a first flow rate F1.

Upon depletion or near depletion of the first medication container 100A, the infusion operation of the first infusion device 1A is stopped and at the same time the infusion operation of the second infusion device 1B is started, which however, at first, takes place at the first flow rate F1 at which the first infusion device 1A was run. This intermediate phase lasts for a predetermined time which is necessary to deliver a residual volume DV remaining in the outlet delivery line 3 towards the patient P (step S2).

After lapse of the predetermined delivery time the second infusion device 1B is switched to the second flow rate F2 and a second fluid from a second medication container 100B of the second infusion device 1B is delivered to the patient P at the second flow rate F2 (step S3).

The idea underlying the invention is not limited to the embodiments described above, but rather can be implemented in an entirely different fashion.

In particular, the invention in principle is not limited to the use of a syringe pump, but can make use also of other infusion devices such as peristaltic (volumetric) infusion devices.

LIST OF REFERENCE NUMERALS 1A, 1B Infusion device
10A, 10B Pump device
100A, 100B Medication container (cylindrical tube)
101A, 101B Actuation device (plunger)
11A, 11B Delivery line (tube set)
12A, 12B Processor
120-122 Communication line
13A, 13B Drive device
2 Relay device
20, 21 Inlet
22 Outlet
3 Outlet delivery line
30, 31 End
300, 310 Asterisk
DV Delivery volume
F1, F2 Flow rate
M1, M2 Medication
P Patient
S1-S3 Method steps

The invention claimed is:

1. A method for performing a continuous infusion process using at least two infusion devices, the method comprising:
delivering a first fluid from a first medication container through a first delivery line at a first flow rate using a first infusion device in a first phase, the first infusion device comprising a processor, and
delivering a second fluid from a second medication container through a second delivery line at a second flow rate using a second infusion device in a second phase following the first phase, the second infusion device comprising a processor separate from the processor of the first infusion device,
wherein a relay device connected to said first delivery line and said second delivery line is configured to receive the first fluid via the first delivery line in the first phase and the second fluid via the second delivery line in the second phase, wherein the relay device is further configured to discharge the received first or second fluid to an outlet delivery line connected to the relay device for administration to a patient, the outlet delivery line having a predefined delivery volume,
wherein subsequent to the delivery of the first fluid using the first infusion device in the first phase, the second infusion device is operated for a predetermined delivery time in an intermediate phase immediately following the first phase to deliver the second fluid at the first flow rate, the intermediate phase including only operation for the predetermined delivery time to deliver the second fluid at the first flow rate, the predetermined delivery time being determined taking the predefined delivery volume of the outlet delivery line into account, and
wherein the first infusion device and the second infusion device communicate from the processor of the first infusion device to the processor of the second infusion device to transfer information concerning the first flow rate, the processor of the second infusion device calculating the predefined delivery time according to the first flow rate and the predefined delivery volume.

2. The method according to claim 1, wherein the predetermined delivery time is determined by a time required to discharge a residual volume of the first fluid from the outlet delivery line.

3. The method according to claim 1, wherein subsequent to the intermediate phase, the second infusion device is operated to deliver the second fluid at the second flow rate.

4. The method according to claim 1, wherein the first fluid and the second fluid comprise an equal medication at a different concentration.

5. The method according to claim 4, wherein in the first phase and in the second phase, a dose rate of the medication is equal.

6. A system for performing a continuous infusion process using at least two infusion devices, the system comprising:
 a first infusion device configured to deliver a first fluid from a first medication container through a first delivery line at a first flow rate in a first phase, the first infusion device comprising a processor,
 a second infusion device configured to deliver a second fluid from a second medication container through a second delivery line at a second flow rate in a second phase following the first phase, the second infusion device comprising a processor separate from the processor of the first infusion device, and
 a relay device connected to said first delivery line and said second delivery line and configured to receive the first fluid via the first delivery line in the first phase and the second fluid via the second delivery line in the second phase, wherein the relay device is further configured to discharge the received first or second fluid to an outlet delivery line connected to the relay device for administration to a patient, the outlet delivery line having a predefined delivery volume,
 wherein the system is configured such that, subsequent to the delivery of the first fluid using the first infusion device in the first phase, the second infusion device is operated for a predetermined delivery time in an intermediate phase immediately following the first phase to deliver the second fluid at the first flow rate, the intermediate phase including only operation for the predetermined delivery time to deliver the second fluid at the first flow rate, the predetermined delivery time being determined taking the predefined delivery volume of the outlet delivery line into account, and
 wherein the first infusion device and the second infusion device are configured to communicate from the processor of the first infusion device to the processor of the second infusion device to transfer information concerning the first flow rate, the processor of the second infusion device being configured to calculate the predefined delivery time according to the first flow rate and the predefined delivery volume.

7. The system according to claim 6, wherein the first infusion device and the second infusion device are in communication connection with each other for controlling the operation of the second infusion device in dependence of the operation of the first infusion device.

8. The system according to claim 6, wherein the first infusion device and the second infusion device are configured to communicate with each other to transfer information concerning:
 the second flow rate,
 a filling level of the first medication container,
 a filling level of the second medication container,
 a start or a stop of an infusion operation,
 a type of fluid delivered during the first phase, and/or
 a type of fluid delivered during the second phase.

9. The system according to claim 6, wherein the first infusion device and/or the second infusion device are configured as a syringe pump.

10. The system according to claim 6, wherein the first medication container and/or the second medication container are configured as a cylindrical tube of a syringe.

* * * * *